(12) United States Patent
Brown et al.

(10) Patent No.: US 7,945,394 B2
(45) Date of Patent: May 17, 2011

(54) DETECTING INCOMPLETE FILL OF BIOSENSORS

(75) Inventors: Daniel V. Brown, Chappaqua, NY (US);
Christina Blaschke, White Pigeon, MI (US)

(73) Assignee: Bayer Healthcare LLC, Tarrytown, NY (US)

( * ) Notice: Subject to any disclaimer, the term of this patent is extended or adjusted under 35 U.S.C. 154(b) by 341 days.

(21) Appl. No.: 11/597,579

(22) PCT Filed: Jun. 16, 2005

(86) PCT No.: PCT/US2005/021708
§ 371 (c)(1),
(2), (4) Date: Sep. 27, 2007

(87) PCT Pub. No.: WO2006/007451
PCT Pub. Date: Jan. 19, 2006

(65) Prior Publication Data
US 2008/0033667 A1    Feb. 7, 2008

Related U.S. Application Data

(60) Provisional application No. 60/580,407, filed on Jun. 17, 2004.

(51) Int. Cl.
*G01F 23/00* (2006.01)
(52) U.S. Cl. .................................................. 702/23
(58) Field of Classification Search .................. 702/23
See application file for complete search history.

(56) References Cited

U.S. PATENT DOCUMENTS

| 5,120,420 | A | 6/1992 | Nankai et al. ............... 204/403 |
|---|---|---|---|
| 5,264,103 | A | 11/1993 | Yoshioka et al. ............ 204/403 |
| 5,320,732 | A | 6/1994 | Nankai et al. ............... 204/403 |
| 5,429,735 | A | 7/1995 | Johnson et al. ............. 204/403 |
| 5,620,579 | A | 4/1997 | Genshaw et al. ............ 204/402 |
| 5,620,890 | A | 4/1997 | Kamps-Holtzapple et al. .......................... 435/345 |
| 5,653,863 | A | 8/1997 | Genshaw et al. ......... 205/777.5 |
| 5,660,791 | A | 8/1997 | Brenneman et al. ........... 422/58 |
| 5,798,031 | A | 8/1998 | Charlton et al. ............. 204/403 |
| 6,129,823 | A | 10/2000 | Hughes et al. ............ 204/403.1 |

(Continued)

FOREIGN PATENT DOCUMENTS

EP    1 262 769 A1    12/2002

(Continued)

OTHER PUBLICATIONS

Yu-Zhi Lam and John Atkinson, Disposable screen-printed biosensor for transcutaneous oxygen measurement, Nov. 4, 2002, Meas. Sci. Technol. 13 (2002) 2074-2081.*

(Continued)

*Primary Examiner* — Tung S Lau
(74) *Attorney, Agent, or Firm* — Nixon Peabody LLP (57) ABSTRACT

A method of detecting incomplete filling of an electrochemical biosensor by collecting a series of electrical current values when a constant electrical potential is applied across the working and counter electrodes during a preliminary burn period. The slope of a line determined by linear regression based on the series of current values is used to determine whether or not the biosensor is incompletely filled. If the line has a positive slope, the biosensor is reported to be under filled. If the slope is not positive, the correlation coefficient of the current values is used as a supplemental test to indicate whether or not the biosensor is incompletely filled.

21 Claims, 4 Drawing Sheets

U.S. PATENT DOCUMENTS

| | | | |
|---|---|---|---|
| 6,531,040 B2 | 3/2003 | Musho et al. | 204/401 |
| 6,576,117 B1 | 6/2003 | Iketaki et al. | 205/777.5 |
| 6,841,052 B2 | 1/2005 | Musho et al. | 204/401 |
| 7,132,041 B2 | 11/2006 | Deng et al. | 205/777.5 |
| 2002/0175075 A1 | 11/2002 | Deng et al. | 204/403.01 |

FOREIGN PATENT DOCUMENTS

| | | | |
|---|---|---|---|
| EP | 1 422 523 A1 | 5/2004 | |

OTHER PUBLICATIONS

Written Opinion corresponding to International Patent Application Serial No. PCT/US2005/021708, European Patent Office, dated Oct. 31, 2005, 5 pages.

International Search Report corresponding to International Patent Application Serial No. PCT/US2005/021708, European Patent Office, dated Oct. 31, 2005, 3 pages.

* cited by examiner

DETECTING INCOMPLETE FILL OF BIOSENSORS

CROSS-REFERENCE TO RELATED APPLICATIONS

This application claims priority to application Ser. No. 60/580,407, filed Jun. 17, 2004, which is incorporated by reference in its entirety.

FIELD OF THE INVENTION

This invention is directed generally to the field of medical devices.

BACKGROUND OF THE INVENTION

More specifically, this invention relates to the biosensors that are used to measure the amount of analytes in bodily fluids, particularly measurements of glucose in samples of whole blood. Optical methods are often used for making such measurements, but the present invention relates to improvements in electrochemical biosensors.

While the method of the invention to be described herein can be applied to measurement of other analytes, including cholesterol, urea, creatinine, and creatine, measuring glucose in whole blood is of particular interest. The invention relates to an electrochemical instrument in which a constant or varying potential is applied to electrodes in contact with a blood sample and the resulting current is measured over a short period of time and then correlated with the amount of an analyte in the sample. Such instruments are referred to as amperometric, in contrast with instruments that measure the total current produced from reaction of the sample and are referred to as coulometric. The amperometric instruments have an advantage in that they carry out their test measurement within a short time compared to those in which the total current produced in oxidizing a sample is measured.

Glucose biosensors of the amperometric type measure the current produced when a fixed potential is applied across a pair of electrodes in contact with a sample of blood. The measured current begins at a high value and then declines and approaches a constant value related to the diffusion of a reduced mediator compound to one of the electrodes for re-oxidation. At a predetermined time, the measured current is used to determine the glucose content of the sample.

The electrodes are generally described as the working electrode (i.e., the electrode at which the mediator is oxidized) and as the counter electrode. Many designs for such biosensors have been described in the art, for example, published U.S. Pat. No. 6,531,040. The electrodes are in contact with a solid layer containing reagents that oxidize the glucose in the sample, such as glucose oxidase and mediators that reoxidize the reduced enzyme. The reduced mediator itself is reoxidized at the working electrode as described above, thereby producing a measurable current, which had been previously correlated with the amount of glucose in the sample being tested. The reactions may be described by the following steps:

Glucose+$E_{oxid}$→$E_{red}$+Oxidized Glucose (Gluconolactone)

$E_{red}$+$n$ Med$_{oxid}$→$n$ Med$_{red}$+$E_{oxid}$ $n$ Med$_{red}$→Med$_{oxid}$+$n$ $e^-$ Where $E_{oxid}$ and $E_{red}$ are oxidized and reduced forms of the redox center of the enzyme and Med$_{oxid}$ and Med$_{red}$ are the oxidized and reduced forms of the mediator.

For measuring glucose, the enzyme may be glucose oxidase and the mediator ferricyanide. Measuring other analytes will employ suitable enzymes and mediators. For example, cholesterol may be measured using cholesterol esterase and ferricyanide, while alcohol may be measured using alcohol oxidase and phenylenediamine. Typical combinations of enzyme, mediator and analyte are listed in Table 1.

TABLE 1

| Analyte | Enzyme | Mediator |
|---|---|---|
| Glucose | Glucose Oxidase | Ferricyanide |
| Glucose | Glucose Dehydrogenase | Ferricyanide |
| Cholesterol | Cholesterol Oxidase | Ferricyanide |
| Lactate | Lactate Oxidase | Ferricyanide |
| Uric Acid | Uricase | Ferricyanide |
| Alcohol | Alcohol Oxidase | Phenylenediamine |

The reagents are supplied in larger amounts than are required in order to make glucose in the blood sample the limiting reaction constituent. It is important that the amount of blood in the sensor be substantially the same from one sensor to another and that each sensor be uniformly filled. But, it has been found that underfilling of biosensors is frequent enough to present a significant problem in assuring consistent and accurate measurements of blood glucose. Clearly, if a person with a diabetic condition must make frequent measurements of his or her blood glucose, it is vital that those measurements be accurate and reliable. Therefore, it is desirable that an amperometric instrument be capable of detecting when a biosensor has been underfilled and is providing an incorrect result, so that the result can be discarded and the test repeated, or the measured current can be adjusted by another algorithm.

Another problem, which was addressed in U.S. Pat. Nos. 5,620,579 and 5,653,863, relates to the premature reducing of the mediator during the period of shelf life before the biosensor is used. If a sample is applied to such a sensor, the reduced mediator will be reoxidized at the working electrode, making it appear that additional glucose was present in the sample, thus giving an incorrect high value. The patentees proposed to begin the test of a sample by providing an initial positive potential pulse for a short period in order to reoxidize any prematurely reduced mediator. Such an initial pulse was referred to as a "burnoff period". The patentees further proposed a method of correcting for the bias introduced by reduced mediator in the sensor. The present invention addresses the data obtained in the burn period as they relate to the filling of biosensors.

In U.S. Pat. No. 6,531,040, an improved amperometric biosensor was described. In one aspect, the biosensor was intended to provide a signal indicating that incomplete filling by the sample had occurred. This was to be accomplished by providing a sub-element of the counter electrode upstream of the working electrode, that is, the sample as it flowed into the sensor by capillary action first reached the working electrode and then the counter electrode. When an underfill condition occurred, the current would be much weaker than would normally be expected and would be recognized as indicating that an underfill had occurred. Another method was described that used measurements of the current during the so-called "read" and "burn" periods to predict that an underfill had occurred. Such methods were also described in U.S. Patent Application Publication No. 2004/0154932.

A general description of the plots of current versus time generated when a constant potential is applied across working and counter electrodes in an amperometric sensor may be helpful to the reader.

In general, when a potential is applied across the working and counter electrodes and a liquid sample of blood or control solution is introduced to the sensor, the dry reagents are rehydrated by the liquid sample and current begins to flow, typically increasing to a peak and then declining over the "burn period," usually about ten seconds in length. During this period the previously reduced mediator is reoxidized, as discussed above, to reduce the bias towards falsely elevated values of glucose content. If a full amount of sample is not present, additional error may be introduced since all of the reagents may not become available for reaction or the working and counter electrodes might not be in complete contact with sample, thus reducing the current during the "burn" period.

After the burn period has been completed, a rest period is provided at a lower potential or at no potential during which the glucose oxidation reactions take place and the mediator is reduced. Then, a constant potential is applied again between the working and counter electrodes and the current is measured for a short period, typically about ten seconds. The current is initially high, but it declines and approaches a constant value that is used to determine the glucose content of the sample. In the methods of the published application and the issued patent referred to above values of the current are taken at certain times in the burn and read periods and used to predict underfilling of the sensor. However, improved methods of predicting underfilling have been sought.

The present inventors have found an improved method of determining underfilling of sensors which will be described below.

SUMMARY OF THE INVENTION

The invention includes a method of determining if an electrochemical biosensor is incompletely filled. A series of electrical current values is taken during a period of time that an electrical potential has been first applied across the working and counter electrodes of the biosensor (i.e., the burn period). The slope of a line determined by linear regression through the series of current values is used to determine whether or not a biosensor is underfilled. The correlation coefficient of the series of current values is used to further refine the determination.

In one embodiment, the method of the invention obtains at least five current values during the "burn" period of time while an electrical potential is applied to the electrodes (e.g., about 10 seconds). Preferably, six current values are selected from the second half of the burn period, which may be from five to ten seconds from the time the sensor is filled with a sample. A linear regression is calculated on these current values as a function of time.

When the slope of the line determined by the linear regression is found to be positive, an underfill condition is reported. Alternatively, if the slope is negative but the correlation coefficient is less than a predetermined value developed from tests on the effect of underfilling on sensor performance, an underfill condition is also reported. The predetermined value of the correlation coefficient will be from about 0.80 to about 0.95. In one preferred embodiment, the correlation coefficient is 0.95.

In one embodiment, the methods of the invention are applied to the amperometric measurement of the glucose content of whole blood.

DETAILED DESCRIPTION OF THE ILLUSTRATED EMBODIMENT

Description of the Preferred Embodiments

The invention will be described below as applied to measuring the glucose content of whole blood, a method of commercial importance. However, the method of the invention has other applications where other analytes such as cholesterol, urea, creatinine, and creatine are found in biological fluids including urine, saliva, and interstitial fluid, where the problem of underfilling of electrochemical sensors is likely to occur.

Electrochemical Biosensors

The present invention is not limited to a particular biosensor design among the many that have been disclosed in the art. An example of biosensors which may be used is described in U.S. Pat. No. 6,531,040, which is illustrated in FIGS. 1 and 2.

Figure 1:
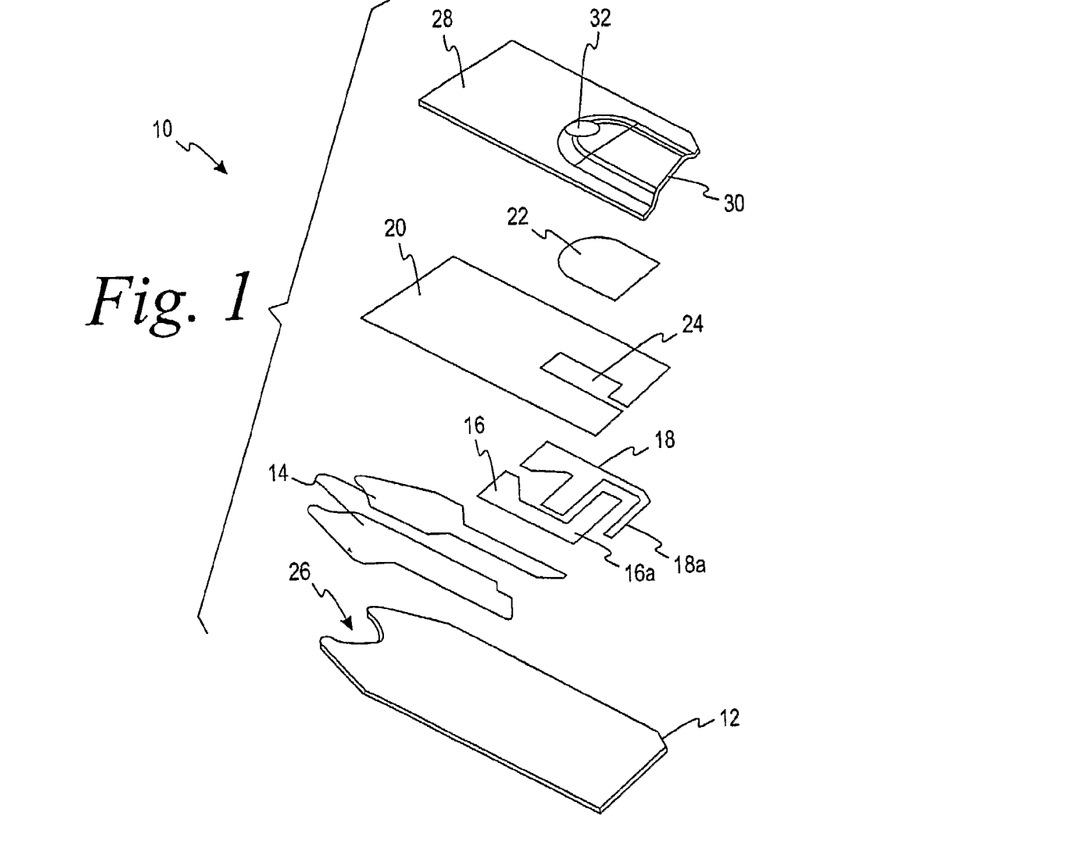
FIG. 1 is an exploded view of a biosensor.
Figure 2:
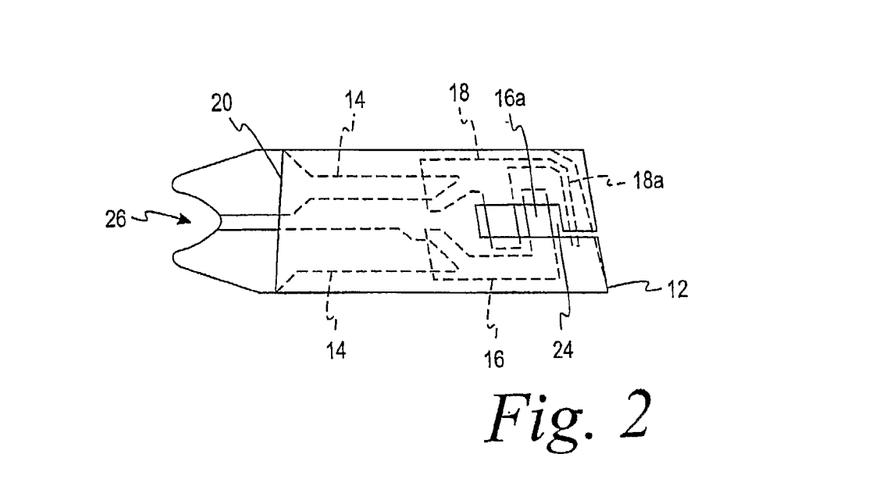
FIG. 2 is an assembled view of the biosensor of FIG. 1.

The biosensor 10 is shown in an exploded view in FIG. 1. It comprises an insulating base 12 upon which is printed in sequence (typically by screen printing techniques), an electrical conductor pattern 14, an electrode pattern (portions 16 and 18), an insulating (dielectric) pattern 20, and a reaction layer 22, and completed by a cover layer 28. The capillary 30 formed between the cover layer 28 and the reagent layer 22, provides a flow path for the fluid test sample. The biosensor is shown in FIG. 2 in which all of the elements on the base are shown in the same plane.

The function of the reaction layer 22 is to effect a chemical reaction with glucose, or another analyte in the fluid test sample, and to produce an electrical current which is measured and correlated with the amount of the analyte present. The reaction layer 22 typically contains an enzyme or enzymes, and an electron acceptor. The enzyme reacts with the analyte to produce electrons, which are conveyed to the surface of the working electrode by an electron acceptor. The electron acceptor may be referred to as a mediator which is reduced in response to the reaction between the analyte and the enzyme. The enzyme in the reaction layer may be combined with a hydrophilic polymer, such as polyethylene oxide. One enzyme that may be used to react with glucose is glucose oxidase and the mediator a ferricyanide salt.

The two portions 16, 18 of the electrode pattern provide the respective working and counter electrodes necessary to electrochemically determine the analyte concentration. A feature of the design shown is that the working and counter electrodes are configured such that the major portion of the counter electrode is located downstream (in terms of the direction of fluid flow along the flow path) from the exposed portion of the working electrode 16*a*.

Counter electrode sub element 18a, however, is positioned up stream from working electrode upper element 16a so that when an amount of the test fluid sample (e.g., a whole blood sample) inadequate to completely cover the working electrode enters the capillary space, an electrical connection forms between counter electrode sub element 18a and exposed portion of the working electrode 16a due to the conductivity of the whole blood sample. The area of the counter electrode, however, that is available for contact by the whole blood sample is so small that only a very weak current can pass between the electrodes and, thus, through the current detector. By programming the current detector to give an error signal when the received signal is below a certain predetermined level, the sensor device informs the user that insufficient blood has entered the sensor's cavity and that another test should be conducted, or that more blood should be added. While the particular dimensions of the electrodes are not critical, the area of the counter electrode sub-element 18a is typically less than about 10% than that of the working electrode and, more specifically, less than about 6%. This element should be made as small as possible.

It was also contemplated in U.S. Pat. No. 6,531,040 that the reaction layer 22 could be removed from contact with counter electrode sub-element 18a, by producing a screen that does not print reagent ink over the counter electrode sub element 18a. This would starve the sub-element for reagent, thereby not allowing it to function as a proper counter electrode, so that an error condition is achieved when the test fluid sample fails to contact the bulk of the counter electrode 18. While sub element 18a is shown as being physically connected to, and therefore part of, the counter electrode 18, 18a may be physically disconnected from the rest of the counter electrode provided that it has its own connector and the sensor is equipped with a third contact to the detector.

The working and counter electrodes are generally printed using electrode ink, which is generally about 14 μm (0.00055") thick and typically contains electrochemically active carbon. Components of the conductor ink may be a mixture of carbon and silver that is chosen to provide a low chemical resistance path between the electrodes and the meter with which they are in operative connection via contact with the conductive pattern at a fish tail end 26 of the sensor. The counter electrode may be comprised of silver/silver chloride although carbon is preferred. To enhance the reproducibility of the meter reading, the dielectric pattern insulates the electrodes from the fluid test sample except in a defined area near the center of the electrode pattern 24. Referring to FIG. 2, a defined area is important in this type of electrochemical determination because the measured current depends not only on the analyte concentration and the area of the reaction layer 22, but also on the area of the working electrode 16a that is exposed to the analyte-containing test sample.

A typical dielectric layer 20 comprises a UV-cured acrylate modified monomer, oligomer or polymer, and is about 10 μm (0.0004") thick. The dielectric layer also may be moisture-curable or heat-curable. A lid or cover 28 is adapted to mate with the base to form a space to receive the fluid test sample in which the counter and working electrodes are situated. The lid 28 provides a concave space 30, and is typically formed by embossing a flat sheet of deformable material. The lid 28 is punctured to provide an air vent 32 and joined to the base 12 in a sealing operation. The lid and base can be sealed together by sonic welding in which the base 12 and lid 28 are first aligned and then pressed together between a vibratory heat sealing member or horn and a stationary jaw. Contact is made only with the flat, non-embossed regions of the lid. Ultrasonic energy from a crystal or other transducer is dissipated as heat in the polymeric joint allowing the bonding of the thermoplastic materials. The embossed lid and base may also be joined by using an adhesive material on the underside of the lid. The method of joining the lid and base are more fully described in U.S. Pat. No. 5,798,031.

Suitable materials for the insulating base 12 include polycarbonate, polyethylene terephthalate, dimensionally stable vinyl and acrylic polymers, and polymer blends such as polycarbonate/polyethylene terephthalate, and metal foil structures (e.g., a nylon/aluminum/polyvinyl chloride laminate). The lid typically is fabricated from a deformable polymeric sheet material such as polycarbonate, or an embossable grade of polyethylene terephthalate, glycol modified polyethylene terephthalate, or a metal foil composition (e.g., an aluminum foil structure).

Other electrochemical sensors may be used in the present invention. Examples of an electrochemical sensor that can be used to measure glucose concentrations are those used in Bayer HealthCare's Ascensia™ DEX® and ELITE® systems. More details on such an electrochemical sensor may be found in U.S. Pat. Nos. 5,120,420 and 5,320,732. Other electrochemical sensors may be purchased from Matsushita Electric Industrial Company. A further example of an electrochemical sensor that may be used in an amperometric monitoring system is disclosed in U.S. Pat. No. 5,429,735.

The electrochemical sensors may be located in a blood glucose sensor dispensing instrument loaded with a plurality of sensors or testing elements. One example of a sensor pack loaded in a sensor dispensing instrument is disclosed in U.S. Pat. No. 5,660,791.

Measuring Glucose in Whole Blood

In a typical biosensor for measuring the glucose content of whole blood, a pair of electrodes, referred to herein as the working electrode and the counter electrode, are coated with a single layer of reagent either by co-printing or co-depositing. The reagent layer will typically include some polymers and the reactive ingredients, that is, an enzyme which oxidizes the glucose in the blood sample and a mediator (i.e., a redox compound that re-oxidizes the enzyme after it has been reduced by oxidizing glucose). The reduced mediator carries electrons from the enzymatic reaction of the glucose oxidation to the working electrode and is re-oxidized at the electrode surface. The applied voltage differential between the two electrodes results in the mediator passing electrons to the working electrode, creating and a measurable current that is proportional to the amount of glucose in the sample. The biosensor also may comprise multiple reagent layers, or may comprise different single or multiple reagent layers at each electrode, working and counter electrodes.

Figure 3:
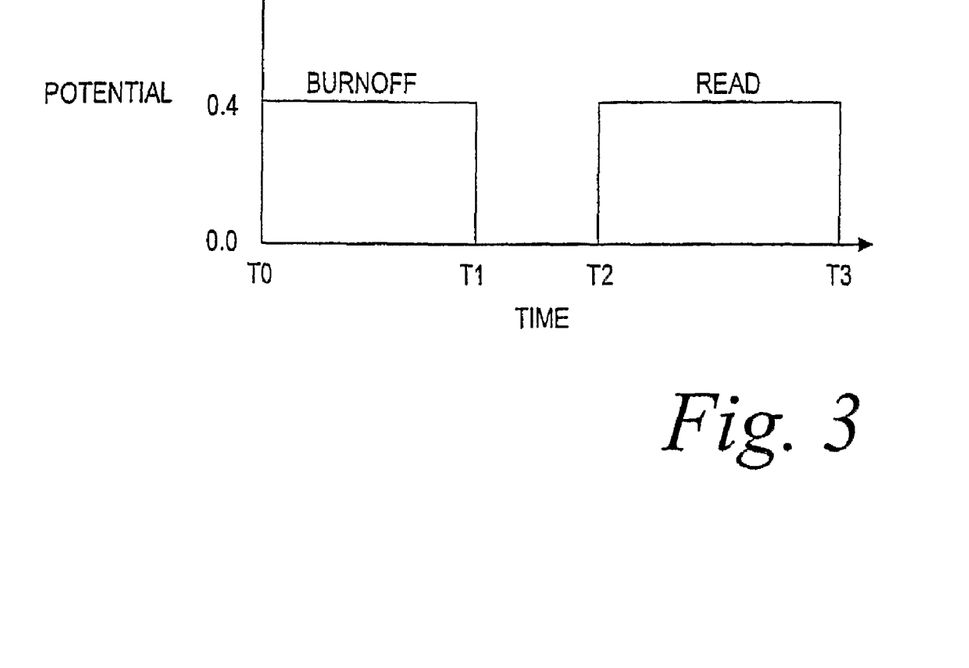
FIG. 3 is a typical plot of the potential applied to amperometric sensors during the burn and read periods.
Figure 4:
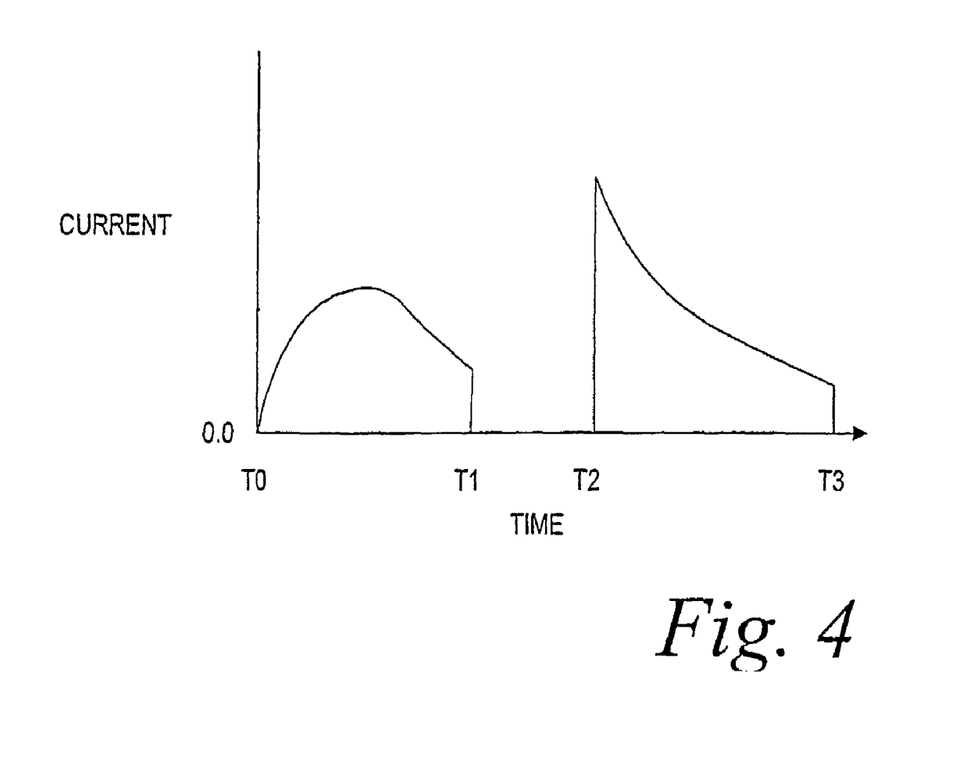
FIG. 4 is a typical plot of the current produced in amperometric sensors during the burn and read periods.

As previously described, the amperometric sensors apply a fixed potential across the electrodes and the current produced is measured over a predetermined period of time, which may be quite short, such as, for example, 5 to 10 seconds, to correct for the bias that may be present due to premature reduction of the mediator. A typical plot of the potential versus time for the "burn period" is presented in FIG. 3. FIG. 4 shows a typical plot of current versus time that results. The current rises to a peak and then declines, while the sample is rehydrating the reagent layer, enabling the oxidation and reduction reactions to occur. After this brief period, the applied potential is removed or at least reduced during a resting period that allows the reactions to occur. Then, the potential is reapplied and the current measured over a predetermined "read" period (e.g., ten seconds). Since reduced mediator is present as the result of the concomitant oxidation of the enzyme, the current produced initially is high, but then it declines asymptotically and approaches a steady state condition. The current recorded at the end of the short "read" period is used to determine the glucose content of the blood sample, through a previously obtained correlation between the current at the end of the read period and the glucose contained in test samples having known concentrations.

Figure 5:
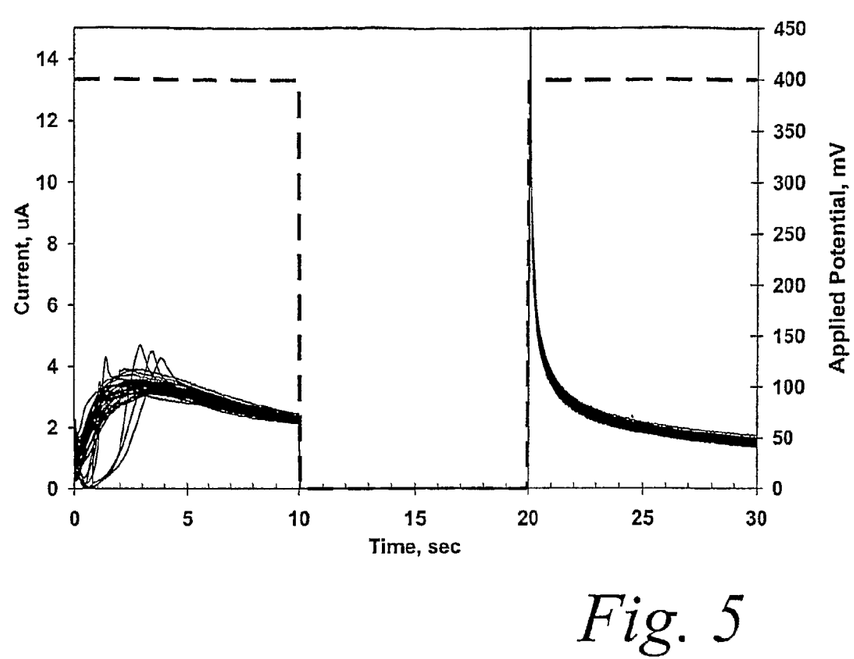
FIG. 5 is a plot of the burn and read periods for multiple sensors that were filled.
Figure 6:
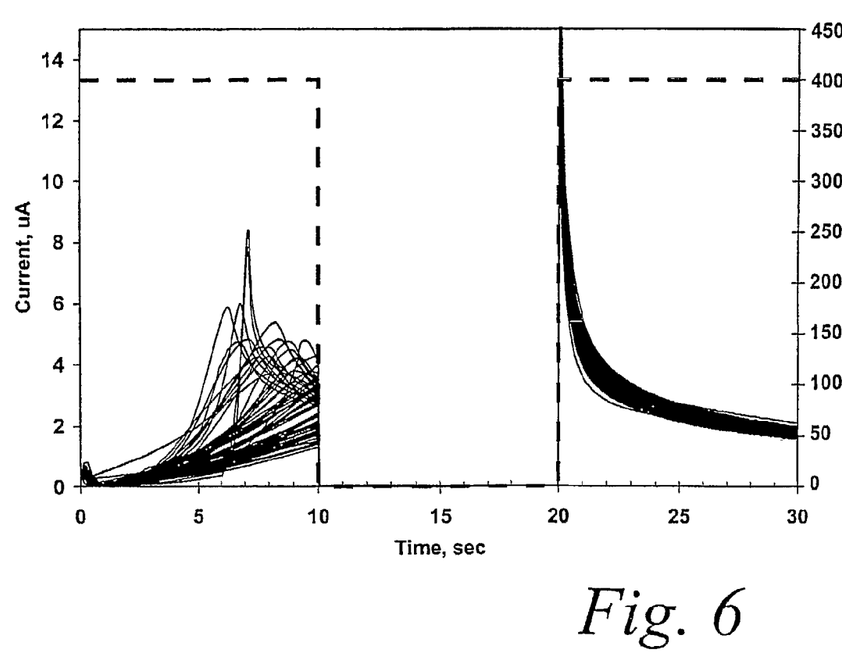
FIG. 6 is a plot of the burn and read periods for multiple sensors that were underfilled.

Previous methods generally employed current flows at predetermined time points in the burn and read periods as indicative of the filling of the sensor, for example the decay factor, k, and the Read-to-Burn ratio, R/B, described in U.S. Patent Application Publication No. 2002/0175075 A1. However, the present inventors discovered that when the biosensor is not filled completely, the current flows during the burn period in particular exhibited very irregular patterns, unlike those shown in FIG. 4. FIGS. 5 and 6 illustrate results the present inventors found. A series of tests with sensors that were not significantly underfilled are shown plotted together in FIG. 5. Aside from minor peaks during the early part of the burn period, the typical pattern of FIG. 4 can be seen. FIG. 6 shows similar plots of tests in which the sensor was intentionally underfilled. The typical pattern of FIG. 4 has disappeared and there is a shift of maximum current flow to the later half of the burn period. These peak shifts are attributed to movement of the sample liquid into the sensor, thereby providing an increase in mediator concentration in the vicinity of the working electrode. In addition, these peak shifts result from insufficient electrode coverage, which delays reagent rehydration and current generation. It follows that selection of any one time during the burn period as an indicator of underfilling is not likely to be sufficient to give reliable results, even though experience has shown that some success has been achieved. In any event, commercial glucose meters do not provide a visual presentation of the current flows and therefore, while observation of the current flows during the burn period is feasible, it is not considered to be a practical way to indicate to the user that underfilling of the sensor has occurred. The present inventors propose a new method which can be provided in commercial glucose sensors using data which is collected during the burn period.

The new method has the following steps:

1. Collect current data at a series of predetermined times during the later portion of the burn period. Preferably, data will be collected at 5, 6, 7, 8, 9, and 10 seconds after beginning the burn period.

2. Determine by statistical methods the best fit of a straight line though the data obtained in the first step, by linear regression. Store the slope of the line and the correlation coefficient.

3. If the slope of the line determined in step 2 is positive, it indicates that underfilling of the sensor has occurred and the user is so informed by the glucose meter. If the slope is not positive, then the correlation coefficient is considered in the next step, since an underfill may still be possible.

4. If the slope of the line from step 2 is not positive, but the correlation coefficient is less than a predetermined value, the user is advised that an underfill is likely and that the procedure should be repeated with a new sensor. The correlation coefficient may be determined from the results of tests made to evaluate the effect of underfilling during the burn period and may vary with the sensor design. The predetermined value of the correlation coefficient is expected to be from about 0.8 to about 0.95. Preferably, for measuring the glucose content of whole blood the predetermined value is 0.95.

If the slope of the line from step 2 is not positive and the correlation coefficient is at or above its predetermined value, preferably 0.95 or higher, the glucose content of the sample is computed from the current recorded at the end of the read step. If below the predetermined value of the correlation coefficient, the result is rejected.

An advantage of the present invention lies in the improved accuracy with which underfilling of the sensor can be determined. Further, the new method involves collecting only a relatively few data points, which is within the capability of current glucose meters because it does not require more sophisticated computational software, does not require a substantial increase in microprocessor memory, and does not significantly decrease battery life. In tests made by the inventors, which will be described more completely below, comparing the method of U.S. Pat. Nos. 5,620,579 and 5,653,863 with the new method it was found that the new method provided improved results. In 1373 sensors known to be underfilled, the new method predicted 80% of the underfills. In contrast, the previous method correctly identified only 47% of the underfills. Furthermore, since the glucose content of the blood samples was known in these tests it was found that, a significant number of the sensors provided glucose readings that were at least 15% too high. Of these, the new method rejected 95%, while the previous method rejected only 60%.

Figure 7:
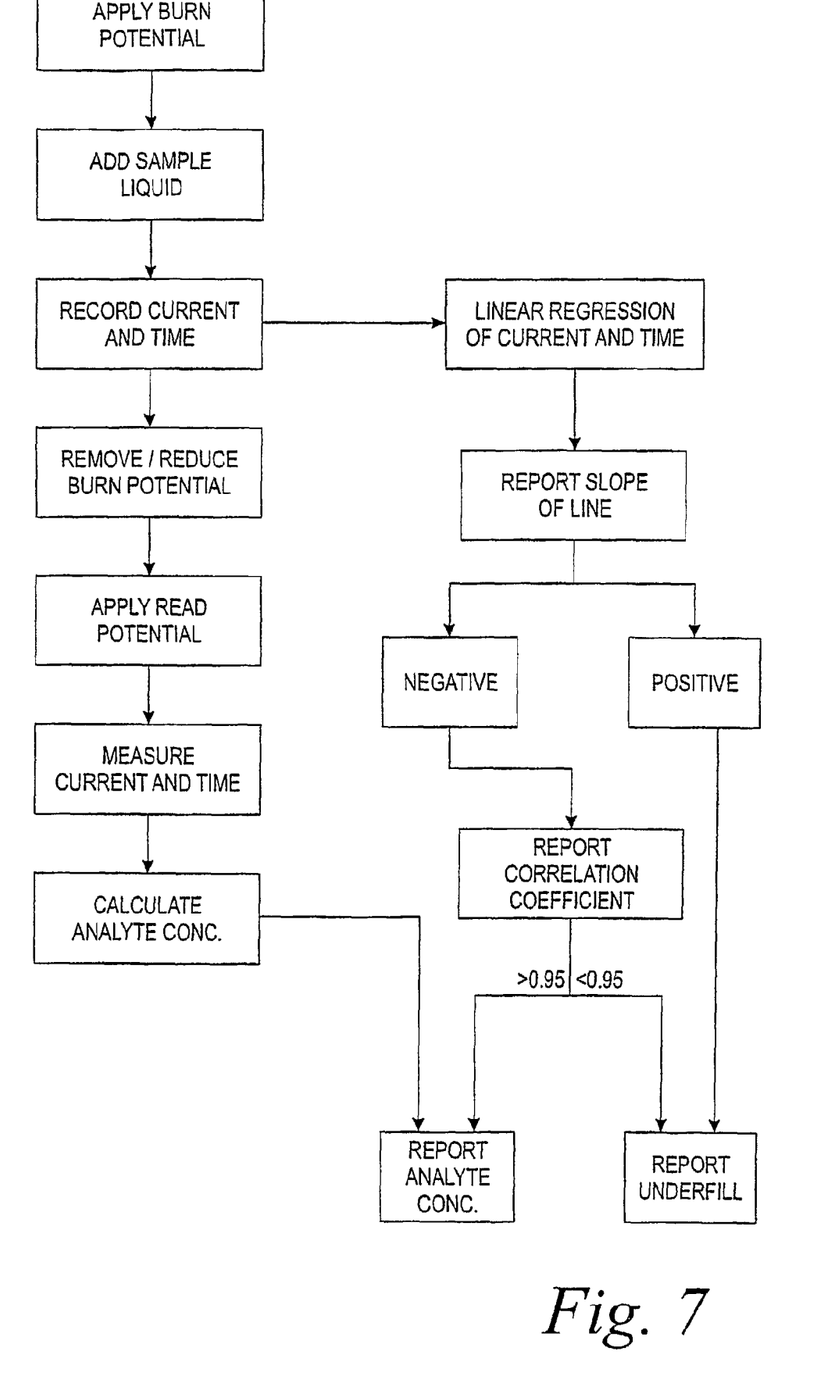
FIG. 7 is a block diagram illustrating the method of the invention.

The method of the invention is illustrated in the block diagram of FIG. 7. The method will be described generally and then as applied to a series of tests carried out by the inventors.

Beginning at the upper left side of the diagram, the first step is to apply an electrical potential, typically about 400 millivolts across the working and counter electrodes of the biosensor. The sample liquid is then introduced to the biosensor to begin the burn period in which the reactive layer is conditioned to improve accuracy of the results. This burn period may be from about 2 to about 10 seconds, typically about ten seconds is used in glucose sensors. The current developed is recorded along with the time for each current value. As will be recalled from FIG. 6, when a sensor is underfilled, the current data may exhibit an erratic pattern during the burn period. In the present invention, it is preferred that data from the latter half of the burn period be selected as indicative of underfilling of the sensor. Thus, it is particularly preferred to take at least 5 data points during the second half of the burn period, especially at least 6 data points. As will be understood from examining FIG. 5, when a biosensor is not underfilled, it would be expected that a line drawn through the second half of the burn period data (current versus time) would have a negative slope, while a line drawn through the second half of the burn period in FIG. 6 was not likely to be negative, but could have a positive slope. Therefore, any line that had a positive slope would be considered to indicate an underfilled sensor and any line that did not show a clearly negative slope could also indicate an underfilled condition. Since rejecting an underfilled sensor is considered important, the criteria used in the invention minimize the possibility that an underfilled sensor was not rejected.

The selected data of current versus time are subjected to linear regression to establish a straight line best fitted to the data. The slope of that line is used as the primary basis for rejecting sensors as being underfilled. That is, when the line has a positive slope, the sensor is reported to be underfilled. To further refine the criteria, the correlation coefficient of the data points is also calculated. If the slope of the line determined is not positive, but not clearly negative, and the correlation coefficient is above a predetermined value (e.g., 0.95 or higher), the sensor is considered to be adequately filled and is so reported. If the correlation coefficient is below the predetermined value (e.g., 0.95) the slope calculation is considered to be questionable. The sensor is reported to be underfilled, although is recognized that some fraction of the sensors might will be rejected unnecessarily.

After the burn period, the instrument used in testing a sample will pause for a rest period in which the electrical potential is removed or at least much reduced, in order for the reactions to occur in the reagent layer. Such periods are typically 0 to about 10 seconds. Following the rest period, the electrical potential is reapplied and the current and time are recorded. The initial current is high, but over the read period, the current declines as it approaches a steady state. After the read period is over, typically about 2 to about 10 seconds, the final current value is used to predict the analyte concentration, such as glucose in milligrams for each deciliter of blood. Previous correlations of current for particular sensors were developed for this purpose. The glucose concentration can be accepted as correct if the sensor is not reported as underfilled using the methods of the invention. Underfilling normally is expected to yield a glucose value that is too high or too low and not to be relied on by a diabetic patient. However, glucose values that are no more than 15% to 20% high or low may be satisfactory if the tests are frequently carried out. Thus, the criteria of the invention are intended also to reject as underfilled those sensors with current profiles that resemble FIG. 6 and that can be expected to report glucose values that are more than 15% high. In a random sample, the actual glucose content would not be known, but in a series of tests carried out by the inventors it was shown that the method of the invention rejected all but 5% of the samples that reported glucose concentrations that were more than 15% higher than the known concentration.

Example

In the tests referred to above, a group of 1373 sensors was intentionally underfilled with blood samples containing known amounts of glucose. Thus, by placing the sensors in a DEX glucose meter (Bayer Corporation) and taking data during the latter portion of burn the period and recording the glucose content read by the meter, the effectiveness of the method of the invention was determined. The protocol of FIG. 7 was followed for each of the 1373 sensors. Since all of the sensors were known to be underfilled, a perfect result would have been to find that all 1373 sensors were underfilled and the glucose reading rejected. In these tests, 80% or 1098 sensors were correctly identified as underfilled. A variance of ±15% from the correct value is acceptable in the context of continuous glucose monitoring and industry standards. Using that standard, it was found that of the 1098 sensors rejected as underfilled, 445 of them still gave glucose readings within 15% of the correct value. Those sensors would require a repeat test, although the results were acceptable. Importantly, about one-half of the sensors gave a glucose reading that was more than 15% above the correct value. Of those 95% were rejected by the protocol of the invention. Taking 687 as the number of erroneous results (i.e., >15% above the correct value), 653 were rejected, a very good result. Thus, only 34 of the sensors out of 1373 would have been missed by the inventive protocol. It can also be concluded that 241 would not have been rejected, but were within the standard for erroneousness, i.e. ±15%, and gave acceptable results.

The series of tests just described showed that the inventive protocol could reject 95% of the sensors that gave incorrect glucose values higher than would be acceptable by the selected standard. It is this ability to reject sensors giving erroneous results that is important to the user. As mentioned above, previous methods were only able to reject about 60% of sensors having erroneous results, thus permitting a much larger number of sensors to be considered as providing accurate results.

What is claimed is:

1. A method of detecting an incomplete filling of a liquid sample in an electrochemical biosensor having working and counter electrodes, the method comprising the acts of:
 (a) applying a constant electrical potential across said working and counter electrodes for a predetermined period of time;
 (b) measuring the current passing between said working and counter electrodes;
 (c) collecting values of the current measured in act (b) at predetermined times during said predetermined period of time of act (a);
 (d) determining by linear regression the slope of a line defined by the values of current collected in act (c); and
 (e) reporting as incompletely filled a biosensor exhibiting a positive slope of a line as determined in act (d).

2. The method of claim 1 further comprising the acts of:
 (f) determining the correlation coefficient of the collected data of act (c);
 (g) reporting as an incompletely filled a biosensor exhibiting a negative slope of a line as determined in act (d) and when the correlation coefficient determined in act (f) is less than a predetermined value.

3. The method of claim 2 wherein said predetermined value is from about 0.80 to about 0.95.

4. The method of claim 3 wherein said predetermined value is about 0.95.

5. The method of claim 1 wherein said collected values are obtained during the second half of said predetermined period of act (a).

6. The method of claim 1 wherein said collected values of act (c) are at least 5 in number.

7. The method of claim 6 wherein said collected values are at least 6 in number.

8. The method of claim 1 wherein said predetermined period of time of act (a) is from about 2 to about 10 seconds.

9. The method of claim 8 wherein said predetermined period of time of act (a) is 10 seconds.

10. The method of claim 1 wherein said biosensor measures the glucose concentration of whole blood.

11. A method of determining an analyte concentration of a fluid sample, the method comprising the acts of:
 providing said fluid sample;
 providing an electrochemical biosensor including a working electrode, a counter electrode, and a reagent;
 placing said fluid sample into contact with said reagent;
 applying an electrical potential across said working and counter electrodes for a predetermined period of time;
 measuring the current passing between said working and counter electrodes;
 collecting values of the measured current at predetermined times during said predetermined period of time;
 determining by statistical methods the slope of a line defined by the collected current values;
 reporting a biosensor as being as incompletely filled if said biosensor exhibits a positive slope of said line defined by the collected current values; and
 if said biosensor is not incompletely filled, determining the analyte concentration of said fluid sample.

12. The method of claim 11 wherein the statistical method is linear regression.

13. The method of claim 12 further comprising the acts of:
 determining the correlation coefficient of the collected values of the measured current;

reporting a biosensor as being incompletely filled if said biosensor exhibits a negative slope of a line and the correlation coefficient is less than a predetermined value.

14. The method of claim 13 wherein said predetermined value is from about 0.80 to about 0.95.

15. The method of claim 11 wherein said collected values are obtained during the second half of said predetermined period.

16. The method of claim 11 wherein said predetermined period of time is from about 2 to about 10 seconds.

17. The method of claim 11 wherein said fluid sample is blood.

18. The method of claim 11 wherein said analyte is glucose.

19. A method of determining of an analyte concentration of a fluid sample, the method comprising the acts of:
   providing said fluid sample;
   providing an electrochemical biosensor including a first electrode, a second electrode, and a reagent;
   placing said fluid sample into contact with said reagent;
   applying a electrical potential across said first and second electrodes for a predetermined period of time;
   measuring the current passing between said first and second electrodes;
   collecting values of the measured current at predetermined times during said predetermined period of time;
   determining the slope of a line defined by the collected current values;
   reporting a biosensor as being as incompletely filled if said biosensor exhibits a positive slope of said line defined by the collected current values; and
   if said biosensor is not incompletely filled, determining the analyte concentration of said fluid sample.

20. The method of claim 19 further comprising the acts of:
   determining the correlation coefficient of the collected values of the measured current;
   reporting a biosensor as being incompletely filled if said biosensor exhibits a negative slope of a line and the correlation coefficient is less than a predetermined value.

21. The method of claim 19 wherein the applied electrical potential is constant.

* * * * *